United States Patent [19]

Stafford et al.

[11] Patent Number: 5,086,233

[45] Date of Patent: Feb. 4, 1992

[54] LUMINOMETERS WITH SAMPLE CONTAINER DISPLACEMENT CONTROLLED BY RAMPED ABUTMENT

[75] Inventors: David A. Stafford, Cardiff; Ian R. Johnson, Mid Glamorgan; Clive Goodfield, Pontypridd, all of United Kingdom

[73] Assignee: Dynatech Corporation, Chantilly, Va.

[21] Appl. No.: 643,493

[22] Filed: Jan. 22, 1991

[51] Int. Cl.⁵ .......................................... G01N 15/06
[52] U.S. Cl. .................................. 250/576; 250/458.1; 356/244
[58] Field of Search ................ 250/207, 239, 361 C, 250/576, 458.1, 461.1, 461.2, 328; 356/244, 317, 318

[56] References Cited

U.S. PATENT DOCUMENTS

| | | | |
|---|---|---|---|
| 4,291,230 | 9/1981 | Heiss | 356/244 |
| 4,319,842 | 3/1982 | Priarone et al. | 356/317 |
| 4,755,055 | 7/1988 | Johnson et al. | 356/440 |

Primary Examiner—Edward P. Westin
Assistant Examiner—John R. Lee
Attorney, Agent, or Firm—Young & Thompson

[57] ABSTRACT

A luminometer comprises a body which is formed with a bore for receiving a sample container and a cavity communicating with the lower end of the bore. A control device having a part-circumferential ramp is rotatable within the cavity for displacing the sample container along the bore to and from a test position in which the sample container is exposed to a photo-multiplier device. The control device is rotated by a cap which is coupled to the control device and which covers the upper end of the bore in light-tight manner as the control device lowers the sample container to the test position.

12 Claims, 2 Drawing Sheets

LUMINOMETERS WITH SAMPLE CONTAINER DISPLACEMENT CONTROLLED BY RAMPED ABUTMENT

INTRODUCTION

This invention relates to luminometers which are devices for measuring light photons, particularly at low light levels, produced by bioluminescent or chemiluminescent effects. The luminometer with which the invention is concerned is designed to detect and measure light emission produced as a result of chemical or other reactions, the measurement being translated into a signal which may take one of many forms, according to particular tests being undertaken.

Typical circumstances in which the luminometer may be used include testing of samples of liquids to determine various factors, and the device may be used in medical applications, in the food and drink, pharmaceutical, water treatment, or other industries. It may also be used for research in various fields.

The luminometer has means for presenting a sample, usually as a liquid or a liquid suspension, to a photo-multiplier device by means of which the actual measurement is carried out.

It may be necessary to prepare the sample before presentation to the photo-multiplier device in various ways, depending upon the nature of the sample and upon the requirements of the test to be conducted. This preparation may include extraction of ATP (adenosine-5'-triphosphate) molecules, adding suitable reagents, or other processes to produce light emissions of sufficient intensity to be detectable and measurable by the photo-multiplier device.

A number of methods have been devised for presenting samples to the photo-multiplier device, which is extremely sensitive and must be screened against extraneous light entry. In EP-A 86309341-5 there is described and claimed a luminometer with automatic handling means for samples, complex mechanisms for rotating a drum, and capability for full computer control. While such a machine is capable of producing very accurate results, it is of a substantial size and is very costly.

There is need in certain industries to provide a luminometer which can be easily used by persons who have substantially no special training for the use of a luminometer, and which may for example provide a simple positive or negative indication. In the sampling of a product such as milk, it may merely be necessary to know if a particular element is present or absent and, if present, whether it is in acceptable or unacceptable quantities.

There are moreover, other circumstances in which an accurate result is required, but conventional desk top, large apparatus which is often linked to a computer is too cumbersome, and is to all intents and purposes static, so that samples for testing have to be brought to it, rather than the machine being taken to the place at which sampling is actually required.

SUMMARY OF THE INVENTION

It is the object of the invention to provide a luminometer which is versatile in that it is of conveniently small size and which, in some circumstances, can be easily used by persons not having specialised knowledge or training, but which is also capable of giving results to a high degree of accuracy.

In accordance with the present invention there is provided a luminometer comprising a body formed with a bore having at one end an entry aperture through which a sample container may be introduced into the bore, a photo-multiplier device remote from said entry aperture, control means for effecting displacement of the sample container along the bore to and from a test position where it is exposed to the photo-multiplier device, and a movable cap which is so coupled to the control means that operation of the control means to displace the sample container to the test position is accompanied by movement of the cap to cover said entry aperture in a light-tight manner.

The cap may constitute an operating member for the control means, whereby the required movement of the control means is effected by moving the cap.

Said bore may be so orientated that the sample container may move downwardly along it under gravity to the test position, said control means including an abutment which may be withdrawn from a position where it initially prevents said downward movement of the sample container to the test position, the abutment being coupled to said cap so that the cap is moved to cover said entry aperture upon withdrawal of the abutment.

The abutment is preferably provided with an inclined upper surface against which the sample container bears, so that withdrawal of the abutment effects gradual lowering of the sample container to the test position.

There may be movable with the abutment a closure part which is normally disposed between the photo-multiplier device and the test position, but which is moved to expose the photo-multiplier device to the test position when the abutment is withdrawn.

The aforesaid cap may include an opening which is normally aligned with said entry aperture and which is moved out of alignment with the entry aperture upon operation of the control means. In the case where the control means include an inclined abutment, the under-surface of the cap may be similarly inclined as it extends away from the opening therein, so as to provide clearance for the upper end of the sample container.

In any of the above arrangements said control means and said cap are preferably rotatable with respect to the body formed with the bore, and are mechanically coupled so that rotation of the control means is accompanied by rotation of the cap. In this case the control means may comprise a part rotatable in a chamber into which the lower end of the bore leads, the part being formed with a part-circumferential ramp against which the lower part of a sample container bears when the container is in the bore, whereby rotation of said part effects lowering or raising of the container in the bore.

The control means and cap are preferably rotatable about an axis parallel to, and spaced from, the axis of the bore. The control means and cap may be disposed at opposite ends of said body, and coupled by a connecting shaft extending through and rotatable in said body.

The invention will now be described by way of example with reference to the accompanying drawings.

DESCRIPTION OF THE PREFERRED EMBODIMENT

Figure 1:
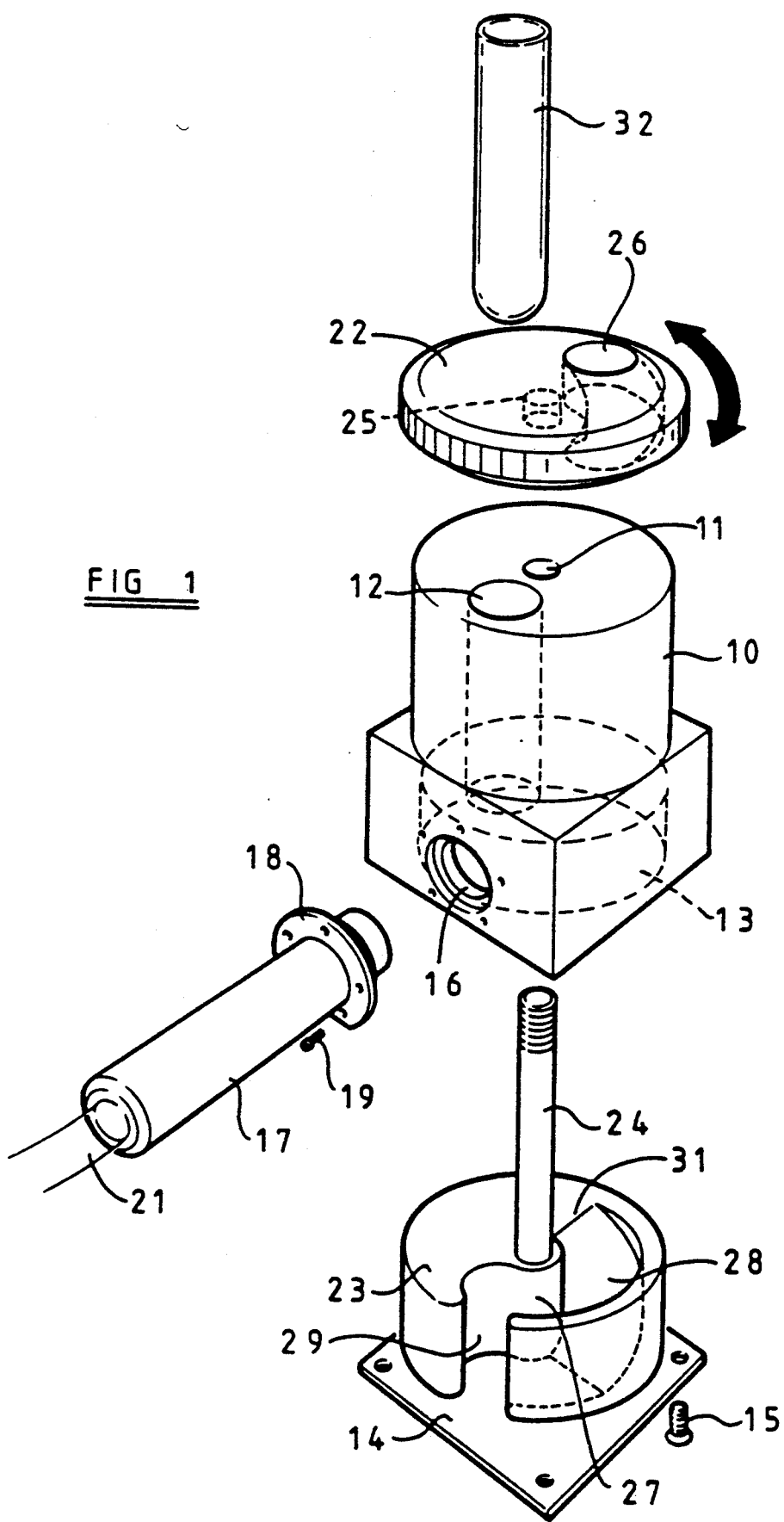
FIG. 1 is an exploded perspective view of a luminometer constructed in accordance with the invention.
Figure 2:
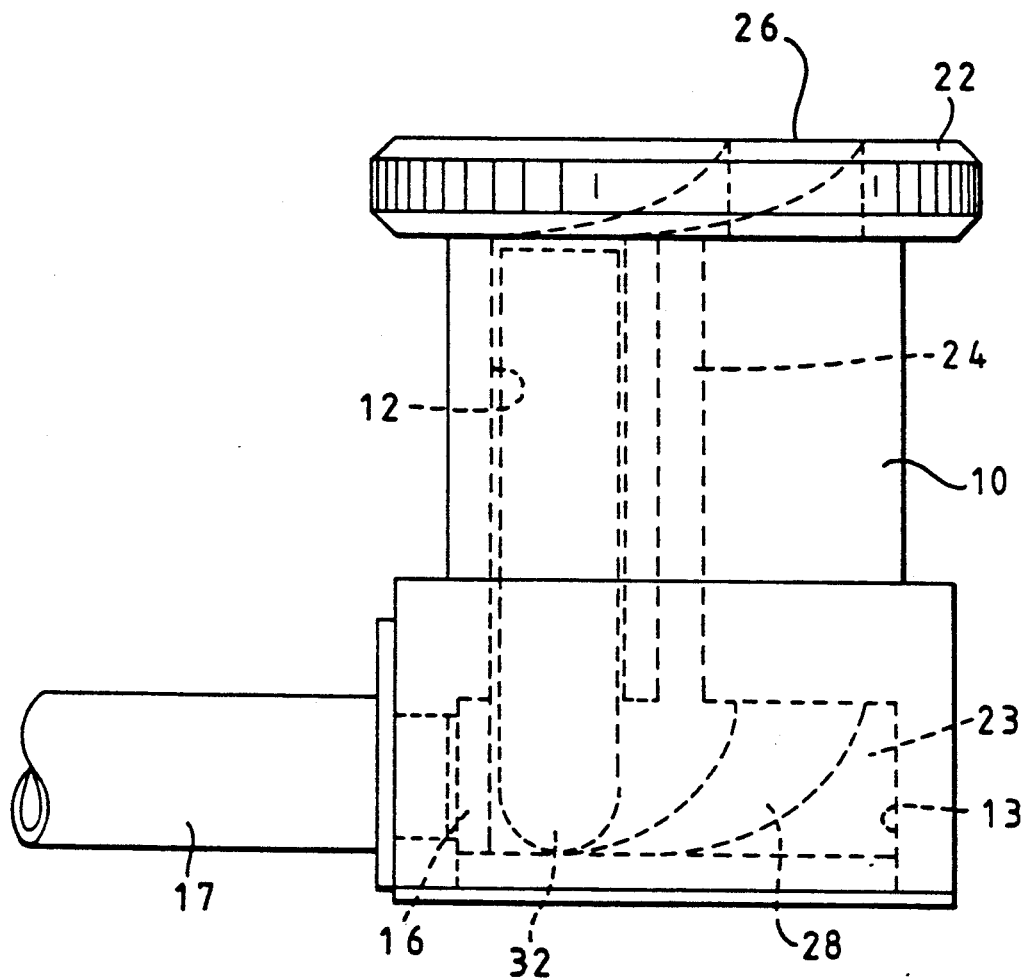
FIG. 2 is a side view of the luminometer.

The luminometer illustrated in the drawings is compact and of a very small size, so that it can be easily carried. It is therefore very convenient to carry out tests in the luminometer at a site where conventional large and complex luminometer machines would be inappropriate, for example where dirty conditions obtain, or where delicate electrical or electronic appliances are at risk of becoming damaged.

In addition to the parts illustrated in FIG. 1, there is a requirement for a power supply, and this may be furnished either by connection to an electrical mains, or through a self-contained power pack of appropriate electrical capacity and preferably of small size.

The luminometer as illustrated comprises a body 10 which includes a base of square section which houses electronic control circuits, and an upper part of generally cylindrical form. The upper part is a solid cylinder, but having a central small bore 11 and a larger bore 12 parallel with the central bore 11 and off-set therefrom. The bore 12 defines, at its upper end, an entry opening which is at the end of the body remote from the base thereof. Within the base of the body 10 there is defined a cylindrical cavity 13 which has an internal diameter approximately equal to the external diameter of the cylindrical upper part of the body 10. The bores 11 and 12 terminate, at their lower ends, in the upper wall of the cavity 13. The cavity is open at its lower end and is normally closed by an end plate 14 securable by screws 15 into the base of the body. The central bore 11 and the off-set bore 12 thus both communicate with the cavity 13, through the upper flat end wall of the cavity.

In one side of the base of the body there is a lateral opening 16 into which is located a photo-multiplier tube 17. A flange 18 on the photo-multiplier tube engages the external surface of the base of the body 10 and is secured thereto by screws 19. An electrical connection to the photo-multiplier tube 17 is indicated at 21. As previously described, this connects with a power supply source. However, electrical connection is also necessary between the photo-multiplier tube 17 and the circuits within the base of the body.

The bore 12 in the body lies on a radial plane which also passes through the lateral opening 16.

Rotatably mounted with respect to the body 10 is an assembly which includes a cap 22 and a part 23 interconnected by a connecting shaft 24.

The cap 22 is circular, having a screw-threaded central blind hole 25 for engagement with the screw-threaded end of the connecting shaft 24. The cap is also formed with an off-set entry opening 26 which is circumferentially elongate at the upper surface. On the lower surface of the cap 22, which rests on the upper flat surface of the base 10, the opening is of greater circumferential extent. The opening 26 in the cover 22 can be placed in register with the opening 12 in the top of the base 10, and because of the shape of the opening 26 within the cap 22, the openings 26 and 12 will remain in communication over a predetermined angle, being rather less than 90°, as the cap is rotated relatively to the base about the central axis represented by the connecting shaft 24. The lower internal surface of the opening 26 in the cap 22 has an inclined ramp-like form.

The connecting shaft 24 is secured in a threaded bore in the part 23, which is itself housed in the cylindrical cavity 13 in the base of the body 10. The part 23 is of generally cylindrical form, but there is a shaped cut-out 27 of part circumferential form. From one end of the cut-out extends an inclined, part-circumferential ramp 28 which is inclined at approximately the same angle as the ramp-like surface within the cap 22.

The ramp 28, however, terminates adjacent, but spaced from, the other end of the part-circumferential cut-out 27. The cut-out has a lateral slot 29 which opens the cut-out 27 to the internal cylindrical side wall of the cavity 13 of the base. In one angular position of the part 23 it is possible to align the slot 29 with the lateral opening 16 in the side of the base of the body 10. The cap 22 can be rotated by hand, and has external knurling to provide a grip. Since the cap is secured by the connecting shaft 24 to the part 23, rotation of the cap is accompanied by rotation of the part 23. The cap 22 and part 23 are inter-related such that the circular entry of the opening 26 is aligned axially with a portion 31 of the top flat surface of the part 23 which is immediately adjacent the upper end of the ramp 28, that is the end of the ramp nearest to the cap 22. The other, lower end of the opening 26 is spaced from a position of axial alignment with the lateral slot 29 in the part 23.

FIG. 1 shows, above the luminometer, a sample container in the form of a transparent, generally cylindrical cuvette 32. The cuvette has an open top, and its lower end is of hemispherical or other convex configuration. The length of the cuvette 32 is equal to, or slightly less than, the distance between the top surface of the cap 22 and the surface portion 31 adjacent the top of the ramp on the part 23.

In use, the cap 22 of the luminometer is rotated to a loading position in which the entry opening 26 in the cap 22 is in alignment with the off-set bore 12 in the body 10. A cuvette is then lowered into the luminometer, to occupy the bore 12, with its lower end resting on the surface portion 31 of the part 23 adjacent the top of the ramp 28.

Anticlockwise rotation of the cap 22, as viewed from above, and also therefore of the connecting shaft 24 and the part 23, will then bring the upper end of the ramp 28 beneath the lower end of the cuvette 32, so that continued rotation allows the cuvette to sink within the bore 12 in the body 10. The shaped underside of the opening 26 in the cap allows clearance for the upper edge of the cuvette as it rotates and sinks. As the cuvette reaches the base of the ramp 28, further rotation of the part 23 brings the slot 29 into alignment with the lower end of the cuvette, placing the cuvette in communication with the photo-multiplier tube 17. This is the operative position.

When the cuvette is in this position, the cap 22 and part 23 are positioned to block any entry of light through the opening 26 in the cap and the bore 12 in the body, since the opening 26 is completely out of register with the bore 12. Sealing surfaces which may include additional sealing gaskets or other provision for excluding light are provided.

It is necessary for the slot 29 in the side of the part 23 to be spaced from the adjacent lower end of the ramp 28 by a distance at least as great as the diameter of the bore 12 in the body 10, so that the cuvette 32 is spaced from the end of the ramp by a distance sufficient to close against the passage of light which could otherwise take place through the bore 12 and opening 26 in the cap 22.

When the cuvette is in the operative position in alignment with the photo-multiplier tube 17, tests may be carried out by energising the photo-multiplier tube. The sample may be prepared in any appropriate way by the addition of reagents or other substances to create a reaction which creates luminescence detectable by the photo-multiplier device.

When a sample in a cuvette 32 has been tested, the cuvette is removed by rotating the cap 22 and part 23 in the clockwise direction, so that the ramp surface 28 again engages the base of the cuvette 32 and lifts the cuvette in the bore 12 until it reaches the initial position on the surface 31 of the part 23, at which time the circular top of the opening 26 in the cap 22 will be aligned with the off-set bore 12 in the body 10. The cuvette can now be lifted out and, if required, another cuvette can be inserted.

The apparatus is therefore extremely simple to operate, and may provide a means of obtaining test results which may be stored in electrical circuits contained within the base of the body 10 of the luminometer for read-out at a later time using appropriate devices. Alternatively, a read-out may be available on the body 10 directly from the circuits contained therein. The read-out may be of numerical or other form or, alternatively, positive or negative readings in the form of different coloured lamps or other devices may represent readings above and below a predetermined threshold. By this means it is therefore possible to test a product by inserting a sample into a cuvette, exposing it to the photo-multiplier tube in the manner described above, and then obtaining a reading indicating whether or not the batch from which the sample has been taken is acceptable or not. The luminometer may however also be adapted to provide results to a high degree of accuracy, if required.

What we claim is:

1. A luminometer comprising a body formed with a bore having at one end an entry aperture through which a sample container may be introduced into the bore, a photo-multiplier device remote from said entry aperture, control means for effecting displacement of the sample container along the bore to and from a test position where it is exposed to the photo-multiplier device, and a movable cap which is so coupled to the control means that operation of the control means to displace the sample container to the test position is accompanied by movement of the cap to cover said entry aperture in a light-tight manner.

2. A luminometer as claimed in claim 1, wherein the cap constitutes an operating member for the control means.

3. A luminometer as claimed in claim 1, wherein said bore is so arranged in use that the sample container may move downwardly along it under gravity to the test position, said control means including an abutment which may be withdrawn from a position where it initially prevents downward movement of the sample container to the test position.

4. A luminometer as claimed in claim 3, further comprising a closure part which is normally disposed between the photo-multiplier device and the test position, but which is movable with the abutment to expose the photo-multiplier device to the test position when the abutment is withdrawn.

5. A luminometer as claimed in claim 3, wherein the abutment is provided with an inclined upper surface against which a sample container bears when the container is in the bore, so that withdrawal of the abutment will effect gradual lowering of the sample container to the test position.

6. A luminometer as claimed in claim 1, wherein the cap includes an opening which is normally aligned with said entry aperture and which is moved out of alignment with the entry aperture upon operation of the control means.

7. A luminometer as claimed in claim 3, wherein the abutment is provided with an inclined upper surface against which a sample container bears when the container is in the bore, so that withdrawal of the abutment will effect gradual lowering of the sample container to the test position and wherein the undersurface of the cap is inclined as it extends away from the opening therein.

8. A luminometer as claimed in claim 1, wherein said control means and said cap are rotatable with respect to the body formed with the bore, and are mechanically coupled so that rotation of the control means is accompanied by rotation of the cap.

9. A luminometer as claimed in claim 8, wherein the other end of the said bore communicates with a chamber, and said control means comprises a part which is rotatable in said chamber.

10. A luminometer as claimed in claim 8, wherein the control means and cap are rotatable about an axis parallel to, and spaced from, the axis of the bore.

11. A luminometer as claimed in claim 8, wherein the control means and cap are disposed at opposite ends of said body, and coupled by a connecting shaft extending through and rotatable in said body.

12. A luminometer comprising a body formed with a bore having at one end an entry aperture through which a sample container may be introduced into the bore, control means rotatable relative to the body for gradually displacing the sample container along the bore to and from a test position, a photo-multiplier device for detecting or measuring light emissions from the sample container when the latter is in the test position, and closure means for closing the entry aperture in a light-tight manner as the control means displaces the sample container to the test position.

* * * * *